United States Patent
Sugimoto et al.

(10) Patent No.: US 9,222,889 B2
(45) Date of Patent: *Dec. 29, 2015

(54) SAMPLE ANALYSIS DEVICE, TESTING APPARATUS, AND SENSOR CARTRIDGE

(71) Applicant: SEIKO EPSON CORPORATION, Tokyo (JP)

(72) Inventors: Mamoru Sugimoto, Chino (JP); Jun Amako, Shiki (JP); Hideaki Nishida, Chino (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,193

(22) PCT Filed: May 2, 2013

(86) PCT No.: PCT/JP2013/002926
§ 371 (c)(1),
(2) Date: Nov. 10, 2014

(87) PCT Pub. No.: WO2013/168404
PCT Pub. Date: Nov. 14, 2013

(65) Prior Publication Data
US 2015/0138543 A1    May 21, 2015

(30) Foreign Application Priority Data

May 11, 2012 (JP) .................. 2012-109188

(51) Int. Cl.
*G01J 3/44* (2006.01)
*G01N 21/65* (2006.01)
*B82Y 15/00* (2011.01)

(52) U.S. Cl.
CPC .............. *G01N 21/658* (2013.01); *G01N 21/65* (2013.01); *B82Y 15/00* (2013.01); *G01N 2201/06113* (2013.01); *Y10S 977/954* (2013.01)

(58) Field of Classification Search
CPC ................ G01N 21/65; G01N 21/658; G01N 2021/656; G01J 3/44; G01J 3/02
USPC ......................................................... 356/301
See application file for complete search history.

(56) References Cited

U.S. PATENT DOCUMENTS 7,079,250 B2   7/2006   Mukai
7,088,449 B1   8/2006   Brongersma
(Continued)

FOREIGN PATENT DOCUMENTS

EP          2372348 A1    10/2011
JP       2000-356587 A    12/2000
(Continued)

OTHER PUBLICATIONS

Du, Lupin, et al: "Localized surface plasmons, surface plasmon polaritons, and their coupling in 2D metallic array for SERS", Optics Express, USA, issued on Jan. 19, 2010, vol. 18, No. 3, pp. 1959-1965.
(Continued)

*Primary Examiner* — Tarifur Chowdhury
*Assistant Examiner* — MD Rahman
(74) *Attorney, Agent, or Firm* — Harness, Dickey & Pierce, P.L.C.

(57) ABSTRACT

A sample analysis device capable of realizing the enhancement of a near-field light while increasing a hotspot areal density is provided. In a sample analysis device, multiple nanostructures are arranged on the surface of a base body. A dielectric body is covered with a metal film in each nanostructure. The nanostructures form multiple nanostructure lines. In each nanostructure line, the nanostructures are arranged at a first pitch SP which is smaller than the wavelength of an excitation light and the nanostructure lines are arranged in parallel with one another at a second pitch LP which is greater than the first pitch SP.

8 Claims, 15 Drawing Sheets

(56) References Cited

U.S. PATENT DOCUMENTS

| | | | |
|---|---|---|---|
| 7,351,588 B2 | 4/2008 | Poponin | |
| 7,399,445 B2 | 7/2008 | Kuroda et al. | |
| 7,483,130 B2 | 1/2009 | Baumberg et al. | |
| 7,733,491 B2 | 6/2010 | Kuroda et al. | |
| 7,768,640 B2 | 8/2010 | Cunningham et al. | |
| 8,085,405 B2 | 12/2011 | Ogawa | |
| 8,093,065 B2 | 1/2012 | Poponin | |
| 8,107,071 B2 | 1/2012 | Kimura | |
| 8,247,216 B2 | 8/2012 | Zaccarin et al. | |
| 2004/0183176 A1 | 9/2004 | Naya et al. | |
| 2005/0067935 A1* | 3/2005 | Lee et al. | 313/309 |
| 2006/0194344 A1 | 8/2006 | Saito | |
| 2007/0090411 A1 | 4/2007 | Naya et al. | |
| 2008/0198376 A1 | 8/2008 | Poponin | |
| 2009/0002701 A1 | 1/2009 | Fattal et al. | |
| 2009/0109422 A1 | 4/2009 | Handa et al. | |
| 2010/0167946 A1 | 7/2010 | Shaw et al. | |
| 2010/0178713 A1 | 7/2010 | Nishiuma et al. | |
| 2010/0233825 A1 | 9/2010 | Yamada et al. | |
| 2010/0309539 A1* | 12/2010 | Kaye et al. | 359/288 |
| 2011/0114859 A1 | 5/2011 | Amako et al. | |
| 2011/0116088 A1 | 5/2011 | Amako et al. | |
| 2011/0164252 A1 | 7/2011 | Handa et al. | |
| 2012/0019828 A1 | 1/2012 | McCaffrey et al. | |
| 2012/0107958 A1 | 5/2012 | Poponin | |
| 2012/0257204 A1 | 10/2012 | Walters | |

FOREIGN PATENT DOCUMENTS

| | | |
|---|---|---|
| JP | 2003-268592 A | 9/2003 |
| JP | 2003-270132 A | 9/2003 |
| JP | 2004-279364 A | 10/2004 |
| JP | 2006-003149 A | 1/2006 |
| JP | 2006-208057 A | 8/2006 |
| JP | 2007-218900 A | 8/2007 |
| JP | 2007-240361 A | 9/2007 |
| JP | 2007-248284 A | 9/2007 |
| JP | 2007-303973 A | 11/2007 |
| JP | 2008-025989 A | 2/2008 |
| JP | 2008-292425 A | 12/2008 |
| JP | 2009-085724 A | 4/2009 |
| JP | 2009-115492 A | 5/2009 |
| JP | 2009-222401 A | 10/2009 |
| JP | 2010-531995 A | 9/2010 |
| JP | 2010-256161 A | 11/2010 |
| JP | 2011-128133 A | 6/2011 |
| JP | 2011-128135 A | 6/2011 |
| JP | 2011-141264 A | 7/2011 |
| JP | 2011-141265 A | 7/2011 |
| WO | WO-2009-002524 A2 | 12/2008 |
| WO | WO-2013-058739 A1 | 4/2013 |

OTHER PUBLICATIONS

Jean Cesario, "Electromagnetic Coupling Between a Metal Nanoparticle Grating and a Metallic Surface", Optical Society of America, Optics Letters, vol. 30, No. 24, Dec. 15, 2005, pp. 3404-3406.

N. Felidj et al., "Enhanced Substrate-Induced Coupling in Two-Dimensional Gold Nanoparticle Arrays", Physical Review B 66, The American Physical Society, 2002, pp. 245407-1 through 245407-7.

Y. Chu et al., "Experimental Study of the Interaction Between Localized and Propagating Surface Plasmons", Optical Society of America, Optics Letters, vol. 34, No. 3, Feb. 1, 2009, pp. 244-246.

M. Inoue et al., "Surface Enhanced Raman Scattering by Metal Spheres, I. Cluster Effect", Journal of the Physical Society of Japan, vol. 52, No. 11, Nov. 1983, pp. 3853-3864.

Y. Chu et al., "Double Resonance Surface Enhanced Raman Scattering Substrates: An Intuitive Coupled Oscillator Model", Optics Express, vol. 19, No. 16, pp. 14919-14928 (Jul. 19, 2011).

Extended European Search Report for Application No. EP 13 77 7779 dated Oct. 20, 2015 (7 pages).

* cited by examiner

SAMPLE ANALYSIS DEVICE, TESTING APPARATUS, AND SENSOR CARTRIDGE

CROSS-REFERENCE TO RELATED APPLICATIONS

This application is a U.S. National Phase Application under 35 U.S.C. 371 of International Application No. PCT/JP2013/002926, filed on May 2, 2013 and published in Japanese as WO 2013/168404 on Nov. 14, 2013. This application is based on and claims the benefit of priority from Japanese Patent Application No. 2012-109188, filed on May 11, 2012. The entire disclosures of the above applications are incorporated herein by reference.

TECHNICAL FIELD

The present invention relates to a sample analysis device including nanobodies covered with a metal film, and a testing apparatus and a sensor cartridge, each utilizing such a sample analysis device, etc.

BACKGROUND ART

There has been known a sample analysis device utilizing localized surface plasmon resonance (LSPR). Such a sample analysis device includes, for example, nanobodies covered with a metal film. The nanobodies are formed sufficiently smaller than, for example, the wavelength of an excitation light. When the metal film on the nanobody is irradiated with an excitation light, all electric dipoles are aligned, and thus an enhanced electric field is induced. As a result, a near-field light is generated on the surface of the metal film. A so-called hotspot is formed.

In "Localized surface plasmons, surface plasmon polaritons, and their coupling in 2D metallic array for SERS", written by Lupin Du, et al., OPTICS EXPRESS, USA, issued on Jan. 19, 2010, Vol. 18, No. 3, pp. 1959-1965, nanobodies are arranged in the form of a lattice at a given pitch. When the size of the pitch is set to a size corresponding to the wavelength of the propagating surface plasmon resonance (PSPR), the enhancement of a near-field light is observed on a metal film on a nanoparticle.

SUMMARY OF INVENTION

Technical Problem

The above-described sample analysis device can be utilized in a testing apparatus for a target substance. As disclosed in NPL 1, when the pitch is set to a size corresponding to the wavelength of the propagating surface plasmon resonance, a hotspot areal density is significantly decreased, and therefore, a target substance cannot easily adhere to the hotspot.

According to at least one aspect of the invention, a sample analysis device capable of realizing the enhancement of a near-field light while increasing a hotspot areal density can be provided.

Solution to Problem (1) One aspect of the invention relates to a sample analysis device including: a base body; and multiple nanostructures, which are arranged on the surface of the base body, and each of which has a dielectric body covered with a metal film, wherein the nanostructures form multiple nanostructure lines, and in each nanostructure line, the nanostructures are arranged in a first direction at a first pitch which is smaller than the wavelength of an excitation light, and the nanostructure lines are arranged in a second direction intersecting the first direction at a second pitch which is greater than the first pitch.

By the action of an excitation light, localized surface plasmon resonance (LSPR) is caused on the metal film of the nanostructure. By the action of the pitch (second pitch) of the nanostructure lines, propagating surface plasmon resonance (PSPR) is caused based on an evanescent wave. The propagating surface plasmon resonance is combined with the localized surface plasmon resonance. A so-called hybrid mode is established. In this manner, the localized surface plasmon resonance is enhanced by the propagating surface plasmon resonance, and the near-field light is enhanced on the metal film of the nanostructure. A so-called hotspot is formed. Moreover, since in each nanostructure line, multiple nanostructures are arranged, the areal density of the nanostructures is increased as compared with the case where a single nanostructure is arranged at a pitch causing resonance with the excitation light. Therefore, the hotspot areal density is increased.

(2) A region which contains no nanostructures may be formed between the nanostructure lines. That is, the formation of nanostructures between the nanostructure lines is excluded. Localized surface plasmon resonance is not induced between the nanostructure lines.

(3) The dielectric bodies of the nanostructures may be formed integrally with the base body. The dielectric bodies of the nanostructures and the base body can be formed from the same material. The dielectric bodies of the nanostructure lines and the base body can be formed by integral molding. The production process of the sample analysis device can be simplified. The mass productivity of the sample analysis device can be increased.

(4) The base body may be formed from a molding material. The dielectric bodies of the nanostructure lines and the base body can be formed by integral molding. The mass productivity of the sample analysis device can be increased.

(5) The metal film may cover the surface of the base body. It is only necessary to uniformly form the metal film on the surface of the base body. Therefore, the production process of the sample analysis device can be simplified. The mass productivity of the sample analysis device can be increased.

(6) In the sample analysis device, a wavenumber at which an intersection is formed between the dispersion relations of the wavelength of a localized plasmon generated in the nanostructures arranged at the first pitch and the metal film may be defined as the second pitch.

(7) The sample analysis device may be utilized by being incorporated into a testing apparatus. The testing apparatus may include the sample analysis device, a light source which emits a light to the nanostructure lines, and a light detector which detects a light emitted from the nanostructure lines according to the irradiation with the light.

(8) Another aspect of the invention relates to a sensor cartridge including: a housing which partitions a detection chamber; a base body which has a surface in contact with a space in the detection chamber; and multiple nanostructures, which are arranged on the surface of the base body, and each of which has a dielectric body covered with a metal film, wherein the nanostructures form multiple nanostructure lines, and in each nanostructure line, the nanostructures are arranged in a first direction at a first pitch which is smaller than the wavelength of an excitation light, and the nanostructure lines are arranged in a second direction intersecting the first direction at a second pitch which is greater than the first pitch.

DESCRIPTION OF EMBODIMENTS

Hereinafter, one embodiment of the invention will be described with reference to the accompanying drawings. The embodiments described below do not unduly limit the contents of the invention described in the claims, and not all the configurations described in the embodiments are essential for the solving means of the invention.

(1) Structure of Sample Analysis Device

Figure 1:
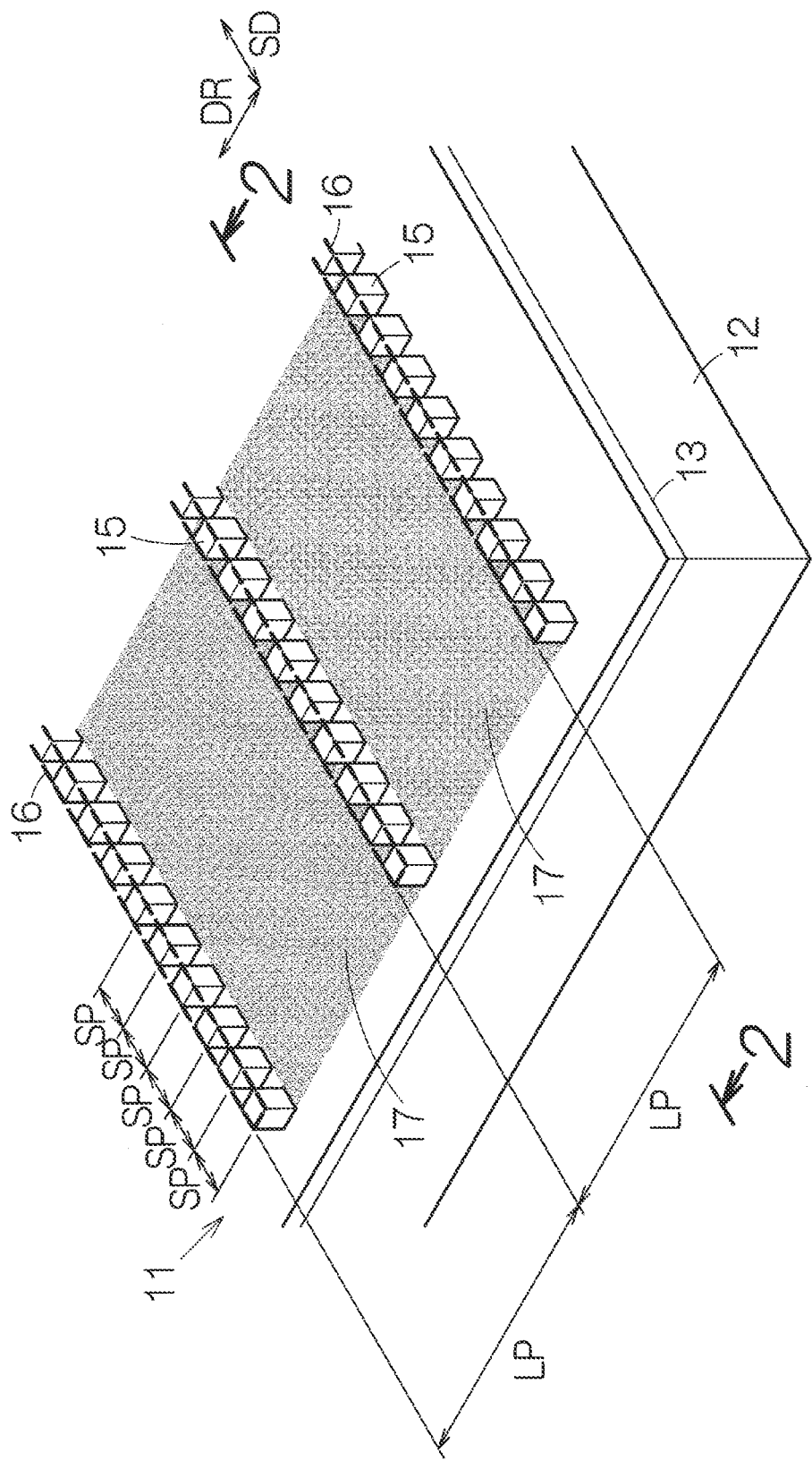
FIG. 1 is a perspective view schematically showing a sample analysis device according to one embodiment of the invention.

FIG. 1 schematically shows a sample analysis device 11 according to one embodiment of the invention. This sample analysis device 11, in other words, a sensor chip, includes a substrate (base body) 12. The substrate 12 is formed from, for example, a molding material. As the molding material, for example, a resin material can be used. The resin material may contain an acrylic resin such as a poly(methyl methacrylate) resin (PMMA resin).

On the surface of the substrate 12, a metal film 13 is formed. The metal film 13 is formed from a metal. The metal film 13 can be formed from, for example, silver. As the metal, other than this, gold or aluminum may be used. The metal film 13 can be continuously formed on, for example, the entire surface of the substrate 12. The metal film 13 can be formed to have a uniform thickness. The thickness of the metal film 13 can be set to, for example, about 20 nm.

On the surface of the metal film 13, nanostructures 15 are formed. The nanostructures 15 protrude from the surface of the metal film 13. The nanostructures 15 are dispersed on the surface of the substrate 12. Each of the nanostructures 15 is formed into a prism. The shape of the horizontal cross section, in other words, the outline of the prism is, for example, a square. The length of one side of the square can be set to, for example, about 1 to 1000 nm. The height of the prism (from the surface of the metal film 13) can be set to, for example, about 10 to 100 nm. The shape of the horizontal cross section of the prism may be a polygon other than the square. The nanostructures 15 may be formed into a cylinder or another three-dimensional shape.

The nanostructures 15 form nanostructure lines 16. In each nanostructure line 16, the nanostructures 15 are arranged in a line at a short pitch SP (first pitch) on the surface of the metal film 13. The nanostructure lines 16 extend in a first direction SD. The short pitch SP is set to be smaller than the wavelength of an excitation light.

The nanostructure lines 16 are arranged in parallel with one another in a second direction DR intersecting the first direction SD at a given long pitch LP (second pitch). Here, the second direction DR perpendicularly intersects the first direction SD in a virtual plane including the surface of the substrate 12. The long pitch LP is set to be greater than at least the short pitch SP. As described later, the size of the long pitch LP is set according to the wavenumber of an evanescent wave.

Between the nanostructure lines 16, a plane region 17 which contains no nanostructures (a region which contains no nanostructures) is formed. That is, the formation of the nanostructures 15 is excluded between the adjacent nanostructure lines 16.

Figure 2:
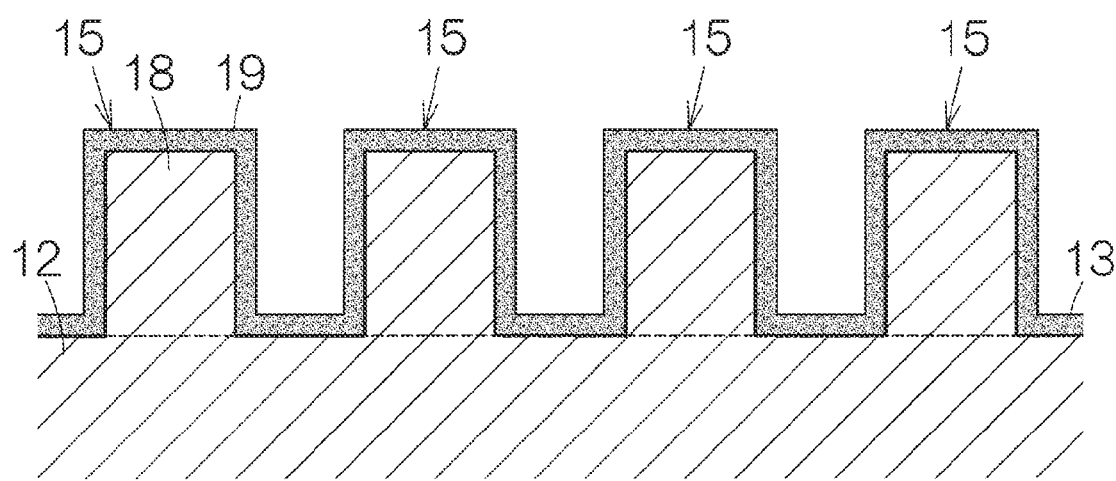
FIG. 2 is a vertical sectional view taken along the line 2-2 in FIG. 1.

As shown in FIG. 2, each nanostructure 15 includes a main body 18 which is a dielectric body. The main body 18 is formed into a prism shape. The main body 18 protrudes from the surface of the substrate 12. The main body 18 can be formed from the same material as that of the substrate 12. The main body 18 can be integrally formed on the surface of the substrate 12.

In each nanostructure 15, the surface of the main body 18 is covered with a metal film 19. The metal film 19 can be formed from the same material as that of the metal film 13. The metal film 19 and the metal film 13 can be formed as one film. The metal film 19 can be formed to have a uniform thickness.

In the sample analysis device 11, the size of each nanostructure 15 is set to be sufficiently smaller than the wavelength of an excitation light. As a result, by the action of the excitation light, localized surface plasmon resonance (LSPR) is caused on the metal film 19 of the nanostructure 15. In addition, when the polarization plane of the excitation light is aligned with the second direction DR, propagating surface plasmon resonance (PSPR) is caused based on the evanescent wave according to the setting of the long pitch LP. The propagating surface plasmon resonance is combined with the localized surface plasmon resonance of the nanostructures 15. A so-called hybrid mode is established. In this manner, the localized surface plasmon resonance is enhanced by the propagating surface plasmon resonance, and the near-field light is enhanced on the metal film 19 of the nanostructure 15. A so-called hotspot is formed. Moreover, in each nanostructure line 16, the interval between the nanostructures 15 is set to be the short pitch SP which is smaller than the long pitch LP, and therefore, the areal density of the nanostructures 15 is increased as compared with the case where the interval between the nanostructures 15 is set to be the long pitch LP.

(2) Verification of Electric Field Intensity

Figure 3A:
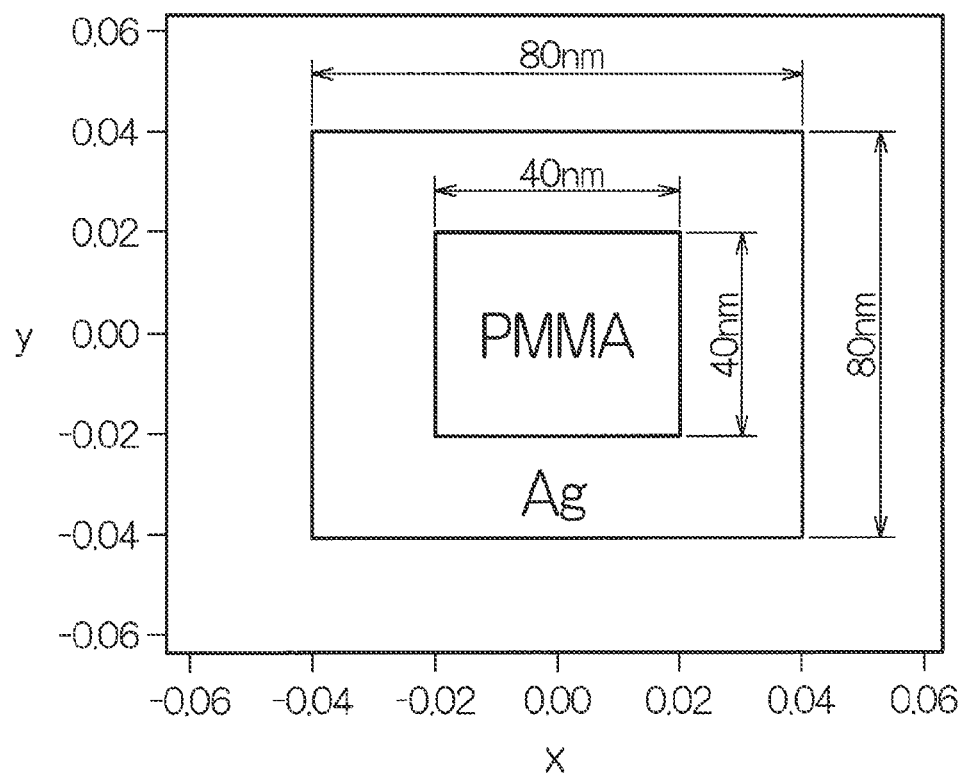
FIG. 3(a) is a plan view and FIG. 3(b) is a side view, each showing a unit of a simulation model.
Figure 3B:
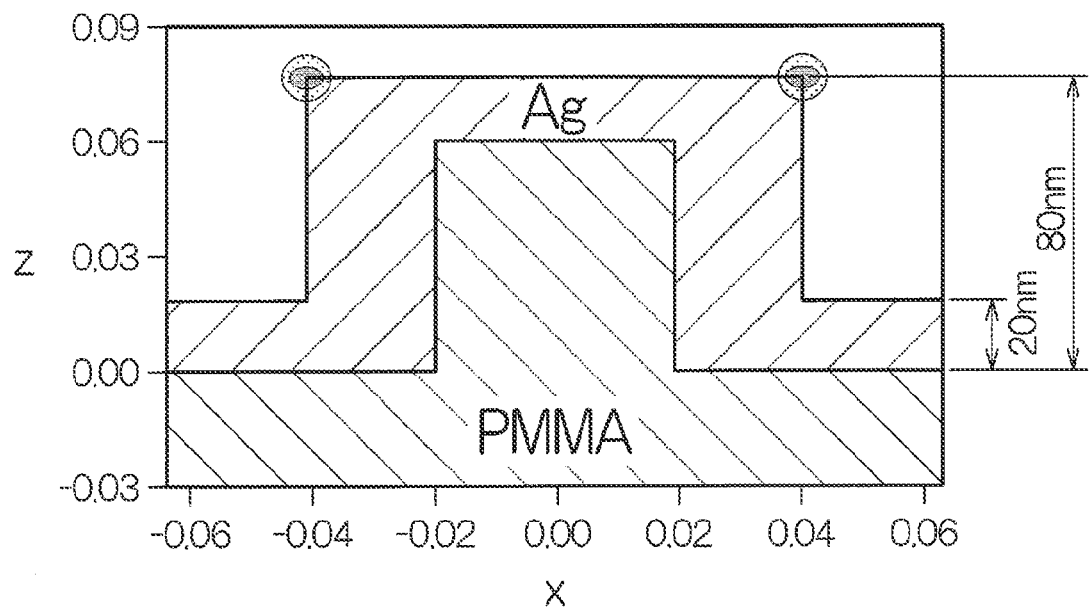

The present inventors verified the electric field intensity of the sample analysis device 11. In the verification, simulation software of an FDTD (Finite-Difference Time-Domain) method was used. As shown in FIGS. 3(a) and 3(b), the present inventors constructed a unit of a simulation model based on a Yee Cell. In this unit, the metal film 13 made of silver was formed on the substrate 12 made of PMMA having a 120 nm square shape. The thickness of the metal film 13 was set to 20 nm. The outline of the main body 18 made of PMMA was set to be a square having a side length of 40 nm. The height of the main body 18 (from the surface of the substrate 12) was set to 60 nm.

Figure 4A:
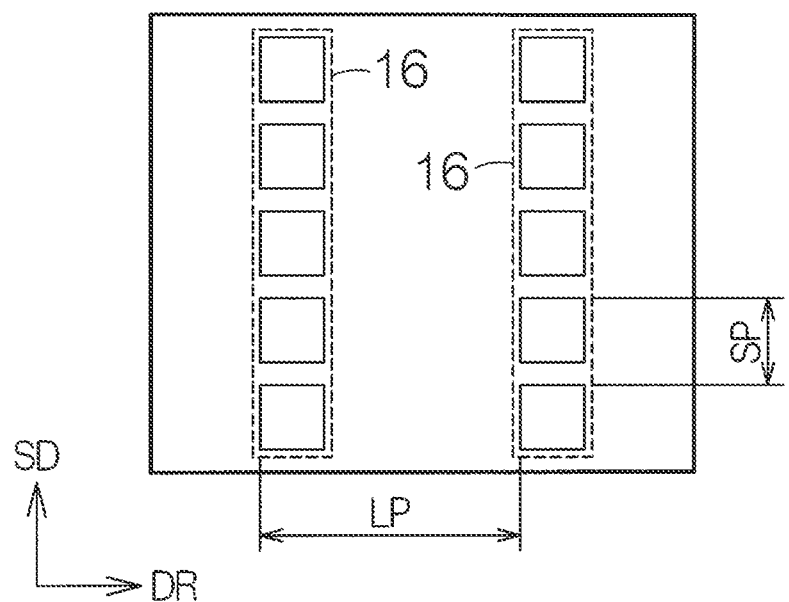
FIG. 4(a) is a plan view of a simulation model according to this embodiment and FIG. 4(b) is a plan view of a comparative simulation model.

As shown in FIG. 4(a), one nanostructure line 16 was constituted by one line of units, that is, the nanostructures 15. Multiple nanostructure lines 16 were arranged parallel to each other. The pitch between the nanostructure lines 16 in the x-axis direction was set to the long pitch LP. As a result, the plane region 17 is formed from a line of void units between the nanostructure lines 16. The void unit is constituted by a void having a 120 nm square shape. An electric field intensity Ex was calculated at the head of the nanostructures 15. A peripheral refractive index ns was set to 1. The excitation light was set to be a linearly polarized light. A polarization plane was aligned with the x-axis direction. The excitation light was set to be vertically incident.

Figure 4B:
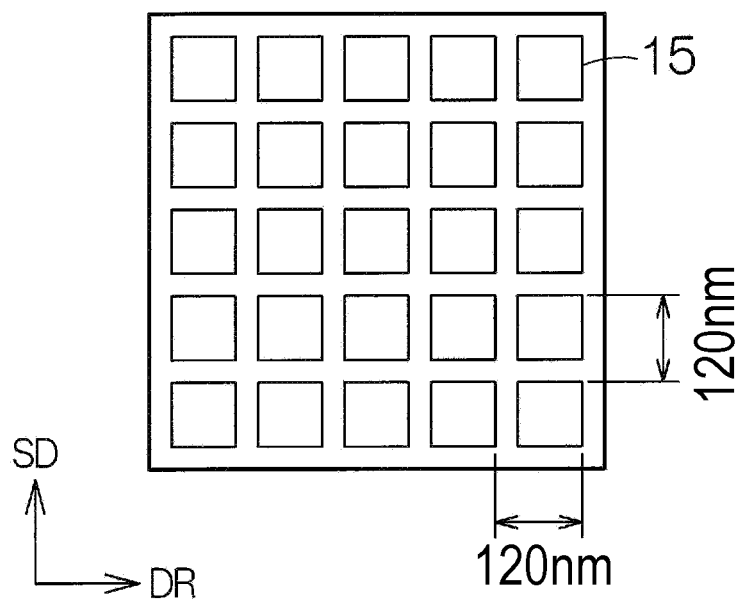

As shown in FIG. 4(b), the present inventors prepared a comparative model. In the comparative model, the long pitch LP was set to 120 nm. That is, the plane region 17 was omitted. Simply, the nanostructures 15 were arranged in the form of a lattice at the short pitch SP. In the same manner as described above, an electric field intensity Ex was calculated at selected one nanostructure 15.

Figure 5:
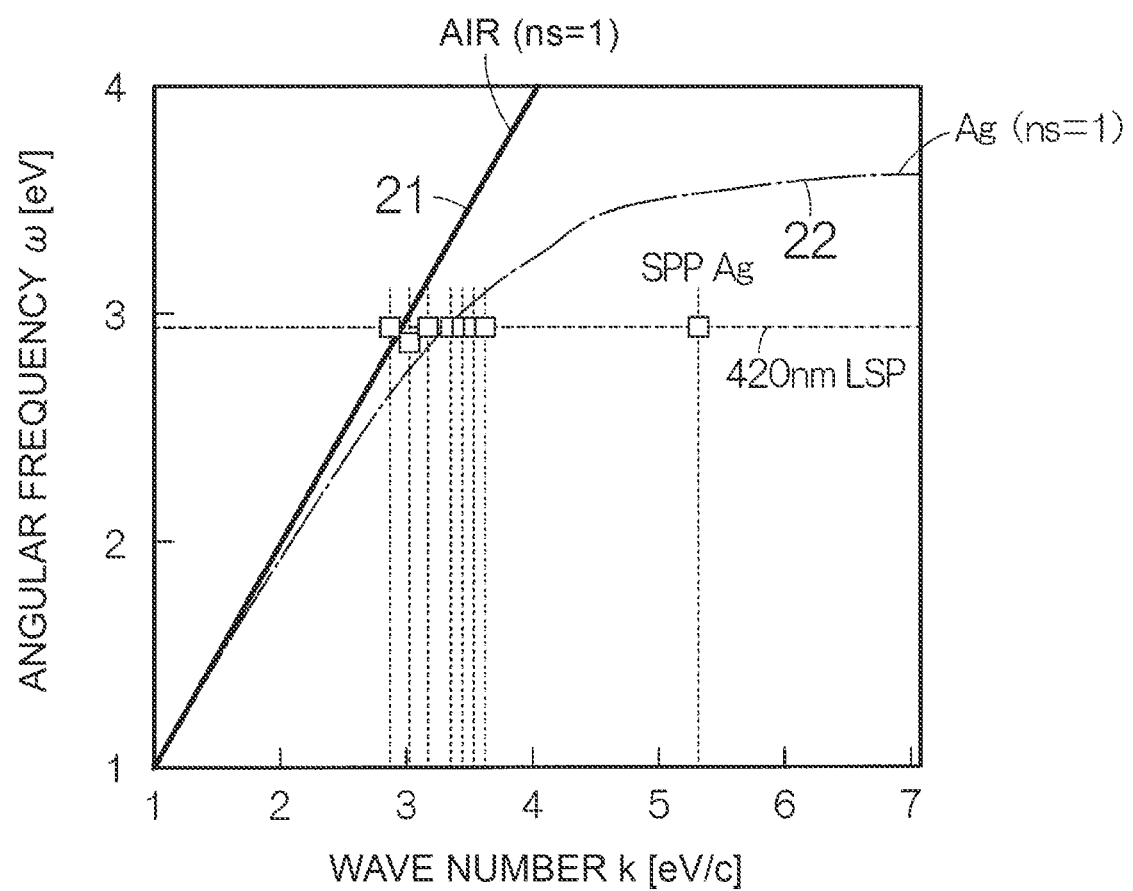
FIG. 5 is a graph showing a dispersion relation prepared based on an electric field intensity.

FIG. 5 shows a dispersion relation prepared based on the electric field intensity Ex. Here, the sum of squares of the electric field intensity Ex converted into a value per unit area was determined. When determining the sum of squares, the electric field intensity Ex was calculated at each of the four corners on the upper side of the nanostructure 15. The square value of the electric field intensity Ex was calculated for each corner, and the square values for all the corners of the minimum unit of repeated calculation were summed. The area of the comparative model was set as a unit area. The summed result was converted into a value per unit area. In this manner, the sum of squares of the electric field intensity Ex per unit area was calculated. A relation between the wavelength of the excitation light and the sum of squares, that is, a frequency characteristic was calculated.

In FIG. 5, the wavenumber k is determined according to the long pitch LP. The straight line 21 represents the dispersion relation of air (ns=1.0). The dispersion relation of air shows a proportional relation. The curve 22 represents the dispersion relation of the propagating surface plasmon resonance of silver Ag having a refractive index (ns=1.0). A wavelength (=420 nm) appearing in common to multiple long pitches LP (=wavenumber k) corresponds to the resonance wavelength of the localized surface plasmon resonance. This is because the inclination of the dispersion relation represents the transfer rate of a propagating surface plasmon, and the inclination of the angular frequency appearing in common to multiple long pitches LP shows 0 (zero). The resonance wavelength of the localized surface plasmon resonance can be determined according to the volume of the nanostructure 15 or the thickness of the metal film 19. A so-called anti-crossing behavior (known as an indicator of a hybrid mode) was not observed.

Figure 6:
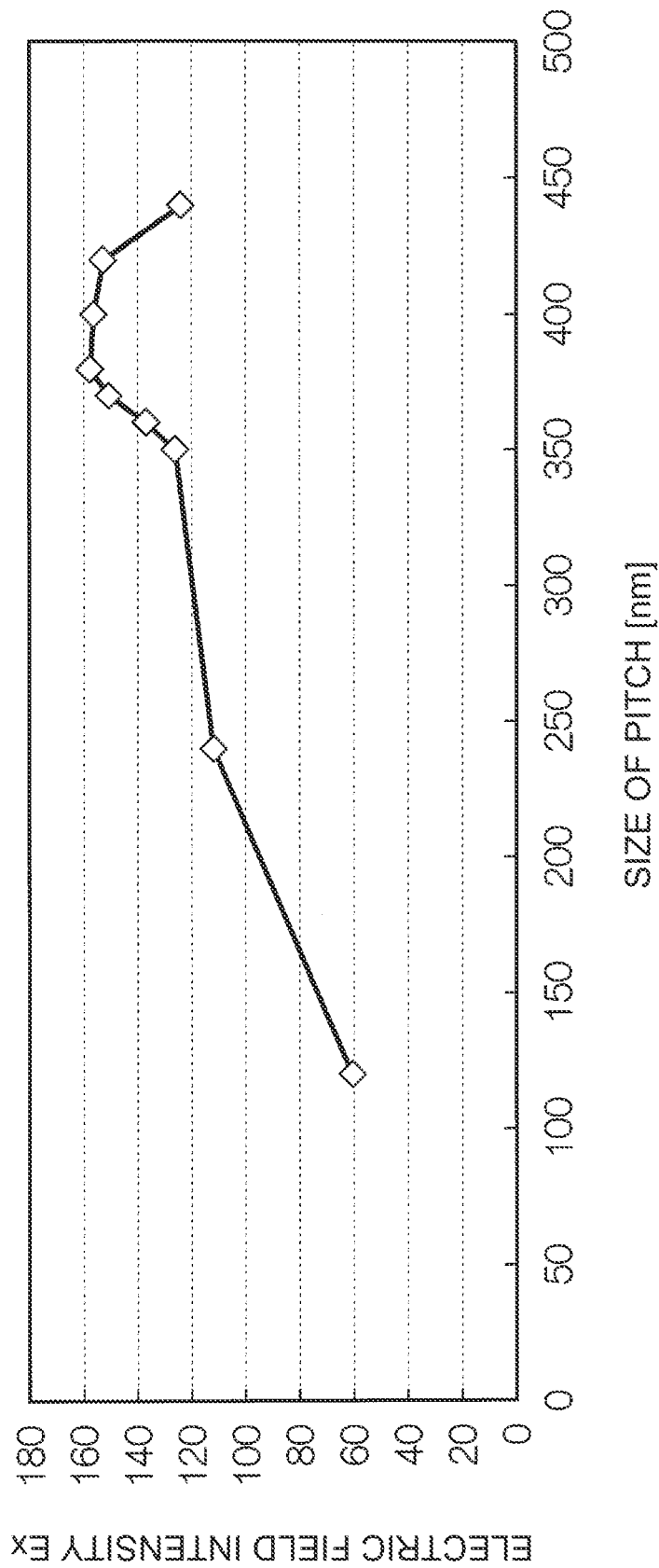
FIG. 6 is a graph showing the maximum value of an electric field intensity.
Figure 7:
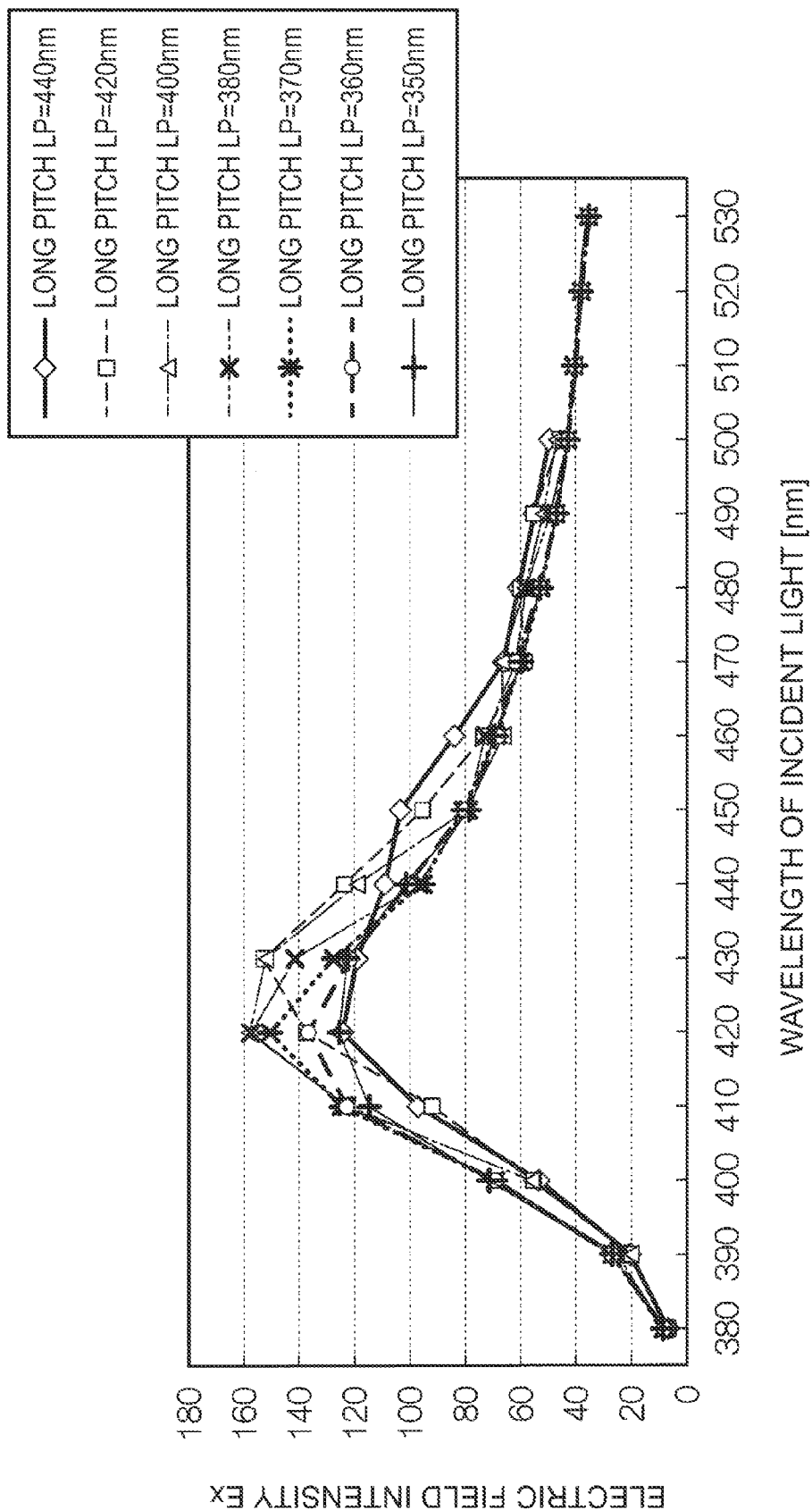
FIG. 7 is a graph showing the wavelength dependence of the maximum value of an electric field intensity.
Figure 8:
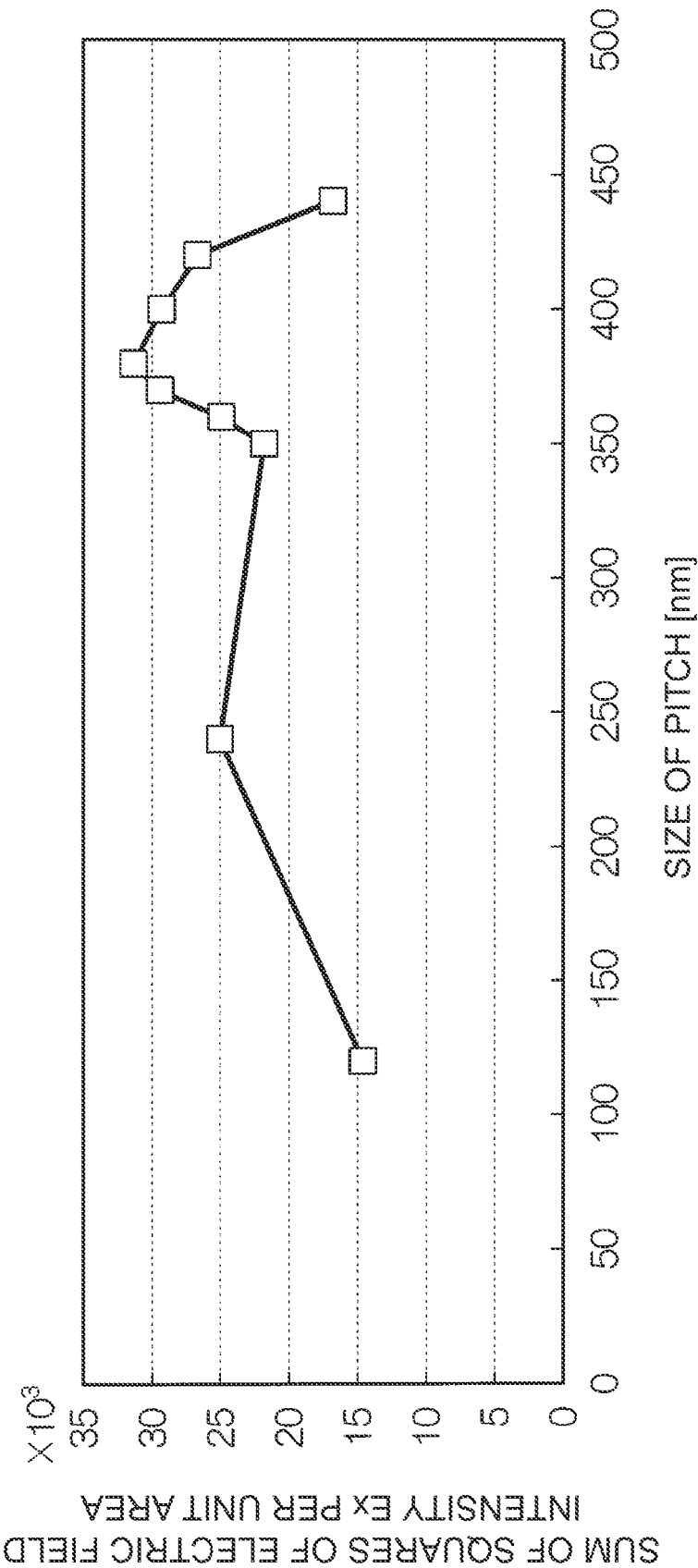
FIG. 8 is a graph showing the sum of squares of an electric field intensity per unit area.

FIG. 6 shows the maximum value of the electric field intensity Ex. It was confirmed that as the long pitch LP is increased as compared with the comparative model, the maximum value of the electric field intensity Ex is increased. In particular, it was confirmed that when the long pitch LP is 380 nm, the maximum value of the electric field intensity Ex shows a peak. As observed from the above-described dispersion relation, the long pitch LP=380 nm corresponds to the intersection point between the dispersion relation of the localized surface plasmon resonance and the dispersion relation of the propagating surface plasmon resonance of silver Ag. FIG. 7 shows the wavelength dependence of the maximum value of the electric field intensity Ex. It was confirmed that regardless of the size of the long pitch LP, the maximum value of the electric field intensity Ex shows a peak at a wavelength of 420 nm. FIG. 8 shows the sum of squares of the electric field intensity Ex per unit area. It was confirmed that as the long pitch LP is increased as compared with the comparative model, the sum of squares of the electric field intensity Ex is increased. In particular, it was confirmed that when the long pitch LP is 380 nm, the sum of squares of the electric field intensity Ex per unit area shows a peak.

Figure 9A:
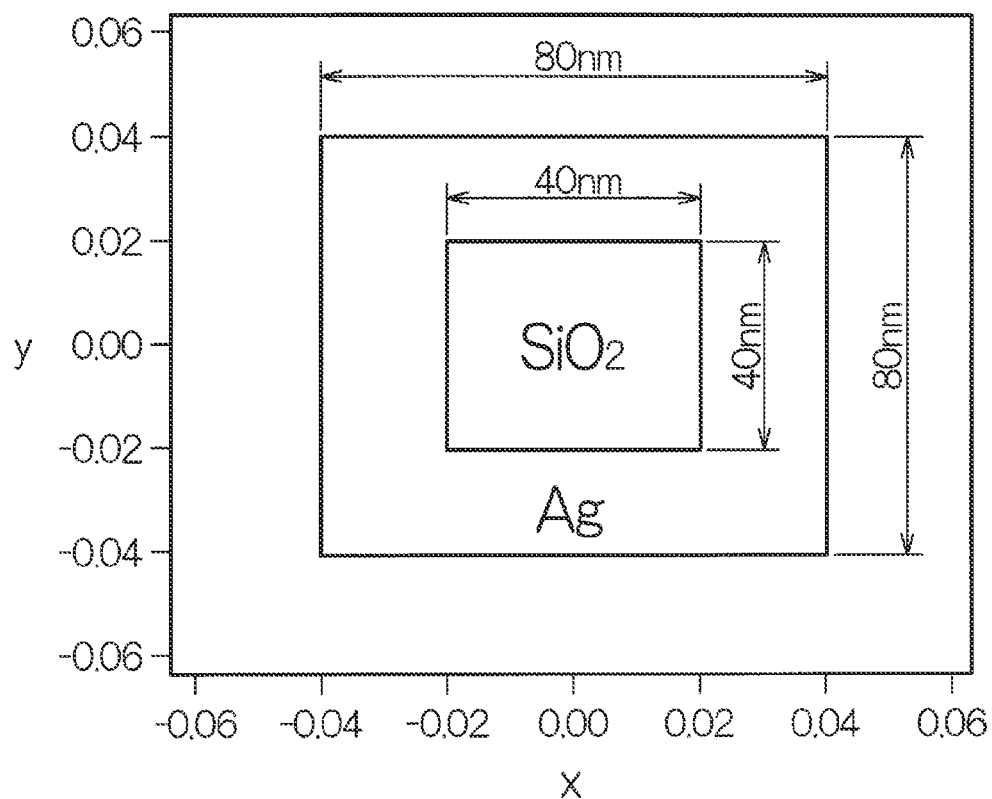
FIG. 9(a) is a plan view and FIG. 9(b) is a side view, each showing a first comparative unit.
Figure 9B:
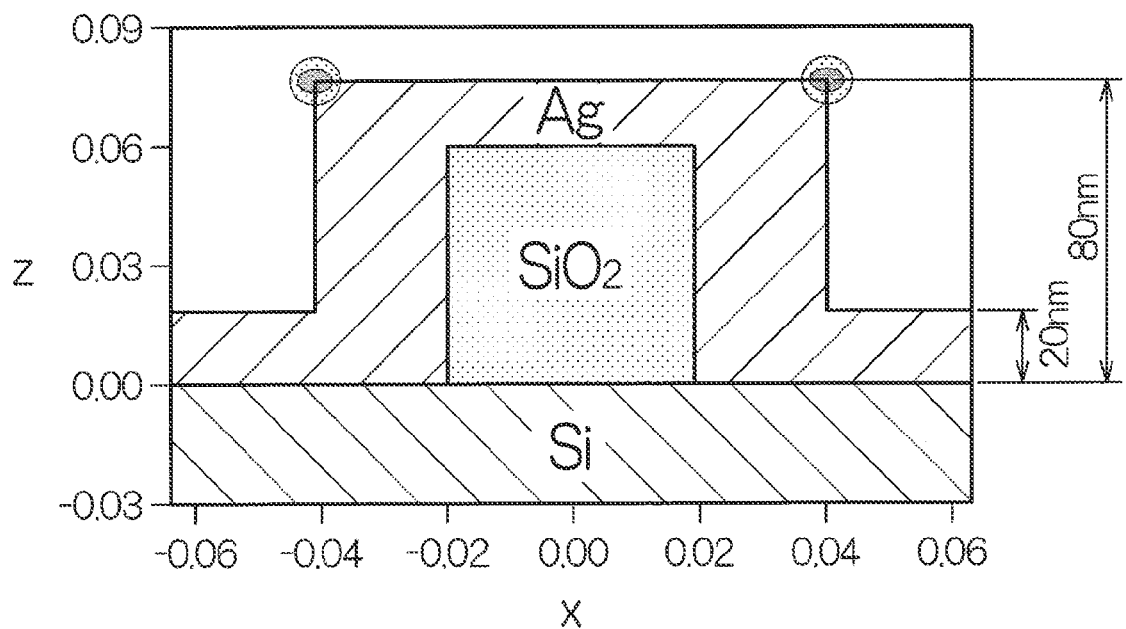

As shown in FIGS. 9(a) and 9(b), the present inventors prepared a first comparative unit. In the first comparative unit, the metal film 13 made of silver was formed on the surface of the substrate 12 made of silicon (Si) having a 120 nm square shape. The thickness of the metal film 13 was set to 20 nm. The main bodies 18 of the nanostructures 15 were formed from silicon dioxide ($SiO_2$). Other structure was formed in the same manner as the unit described above.

The present inventors prepared a second comparative unit in the same manner. In the second comparative unit, the metal film 13 made of silver was formed on the surface of the substrate 12 made of silicon dioxide ($SiO_2$) having a 120 nm square shape. The thickness of the metal film 13 was set to 20 nm. The main bodies 18 of the nanostructures 15 were formed from silicon dioxide ($SiO_2$). That is, the main bodies 18 of the nanostructures 15 and the substrate 12 were designed to have an integral structure. Other structure was formed in the same manner as the unit described above.

Figure 10:
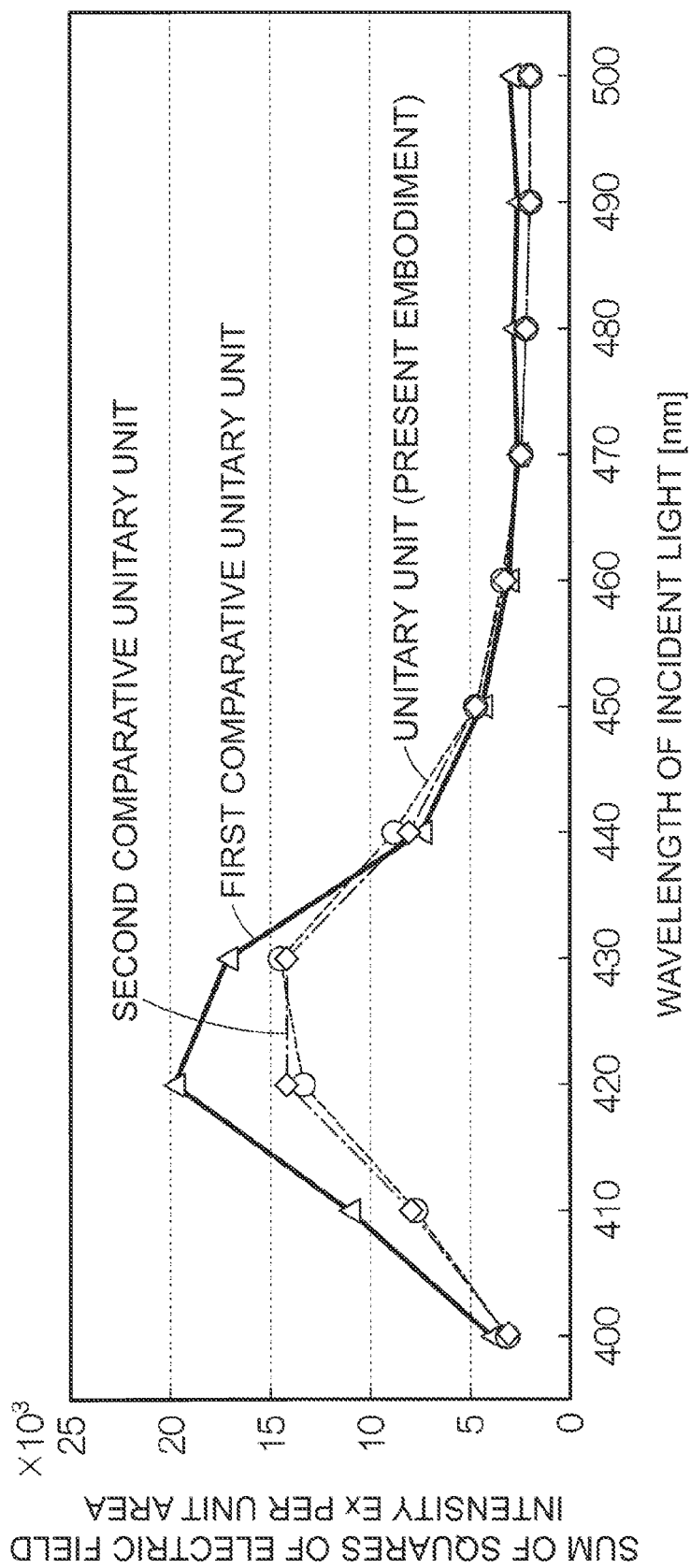
FIG. 10 is a graph showing the wavelength dependence of an electric field intensity.

FIG. 10 shows the wavelength dependence of the electric field intensity Ex. When determining the wavelength dependence, comparative models were constructed with the unit, the first comparative unit, and the second comparative unit. The sum of squares of the electric field intensity Ex per unit area was calculated in the same manner as described above for each wavelength of the excitation light with the comparative models. At this time, the refractive index of silicon dioxide was set to 1.45, and the refractive index of PMMA was set to 1.48. As apparent from FIG. 10, the enhancement of the electric field intensity Ex was observed in the first comparative unit with respect to the unit and the second comparative unit. Almost no difference in the electric field intensity Ex was observed between the unit and the second comparative unit. Based on these results, it can be easily inferred that in the first comparative unit, the electric field intensity Ex was enhanced by the effect of a returning light reflected from the surface of the substrate 12 made of silicon. On the other hand, when the main bodies 18 of the nanostructures 15 and the substrate 12 are integrally formed, the main bodies 18 of the nanostructures 15 and the substrate 12 can be formed from the same material. The main bodies 18 of the nanostructures 15 and the substrate 12 can be formed by integral molding. The production process of the sample analysis device 11 can be simplified. The mass productivity of the sample analysis device 11 can be increased. When performing integral molding, the nanostructures 15 and the substrate 12 may be formed from a molding material.

(3) Production Method for Sample Analysis Device

Figure 11:
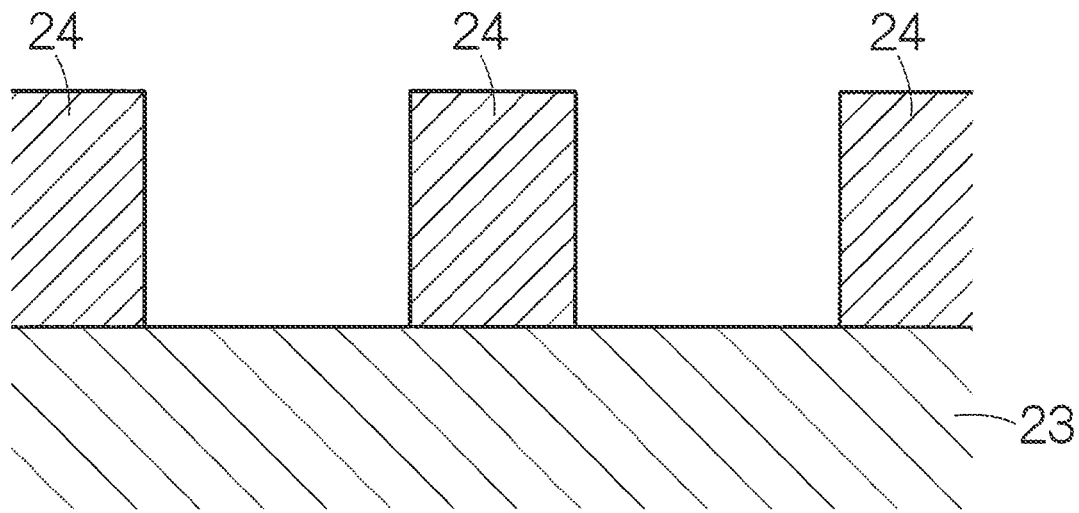
FIG. 11 is a sectional view schematically showing protrusions formed on the surface of a silicon substrate.

Next, a production method for the sample analysis device 11 will be briefly described. When producing the sample analysis device 11, a stamper is produced. As shown in FIG. 11, protrusions 24 made of silicon dioxide ($SiO_2$) are formed on the surface of a silicon (Si) substrate 23. The surface of the silicon substrate 23 is formed as a smooth surface. Each protrusion 24 has a shape corresponding to the main body 18 of the nanostructure 15 to be dispersed on the surface of the substrate 12. When forming the protrusions 24, for example, a lithographic technique can be used. A silicon dioxide film is formed on the entire surface of the silicon substrate 23. A mask patterned with the main bodies 18 of the nanostructures 15 is formed on the surface of the silicon dioxide film. As the mask, for example, a photoresist film may be used. When the silicon dioxide film is removed around the mask, the respective protrusions 24 are formed from the silicon dioxide film. When forming the protrusions at this time, an etching treatment or a milling treatment may be performed.

Figure 12:
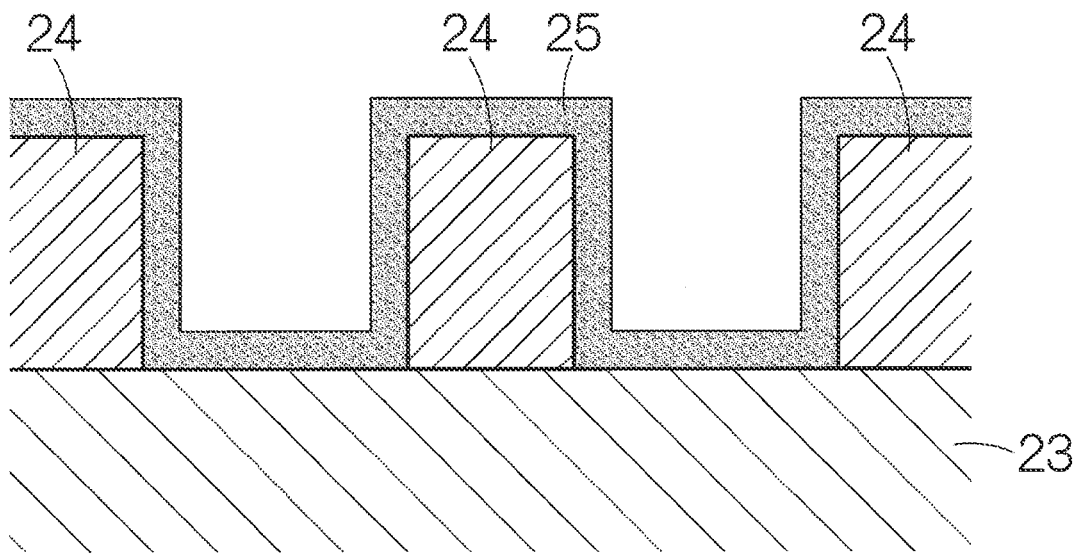
FIG. 12 is a sectional view schematically showing a nickel film formed on the surface of a silicon substrate.
Figure 13:
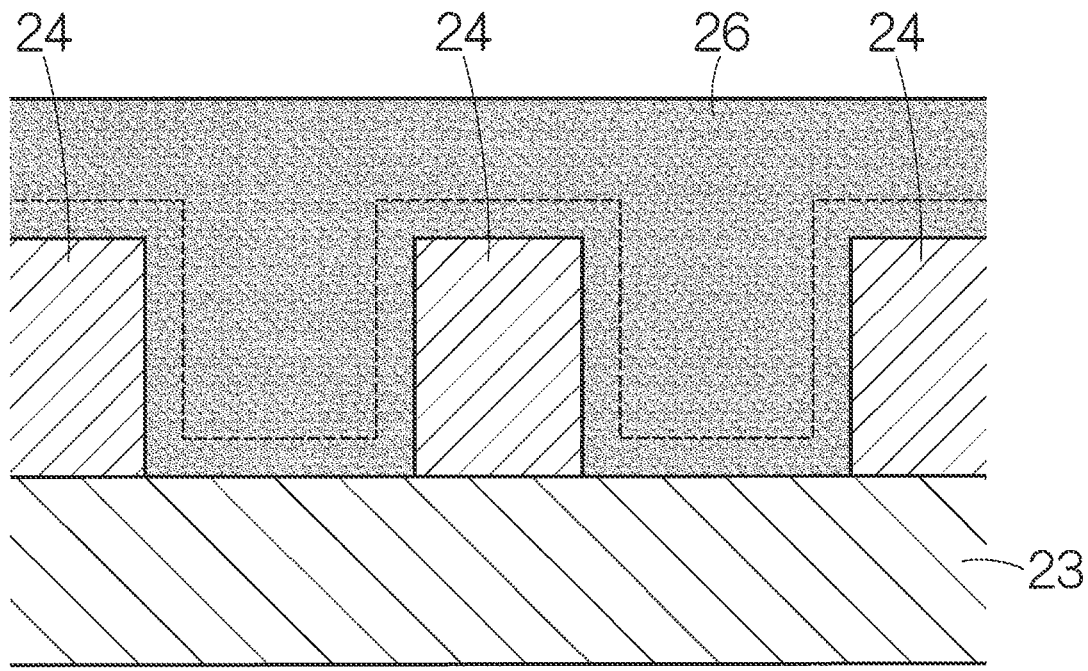
FIG. 13 is a sectional view schematically showing a nickel plate formed on the surface of a silicon substrate.
Figure 14:
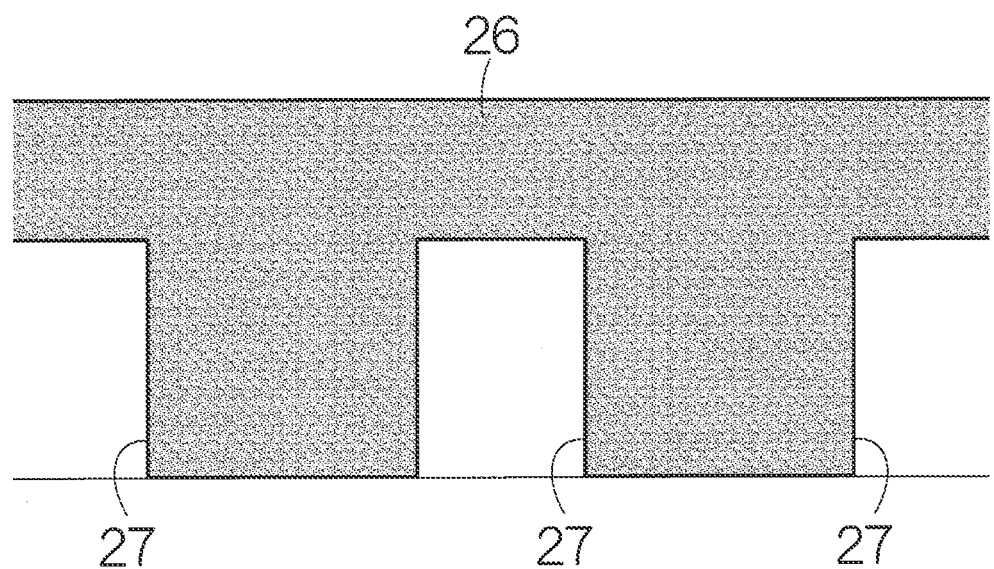
FIG. 14 is a sectional view schematically showing the nickel plate detached from the silicon substrate.

As shown in FIG. 12, a nickel (Ni) film 25 is formed on the surface of the silicon substrate 23. When forming the nickel film 25, electroless plating is performed. Subsequently, as shown in FIG. 13, electroforming is performed based on the nickel film 25. On the surface of the silicon substrate 23, a thick nickel plate 26 is formed. Thereafter, as shown in FIG. 14, the nickel plate 26 is peeled off from the silicon substrate 23. In this manner, a stamper made of nickel can be produced. The surface of the nickel plate 26, that is, the stamper is formed into a smooth surface. On the smooth surface, as the peel-off marks of the protrusions 24, recesses 27 are formed.

Figure 15:
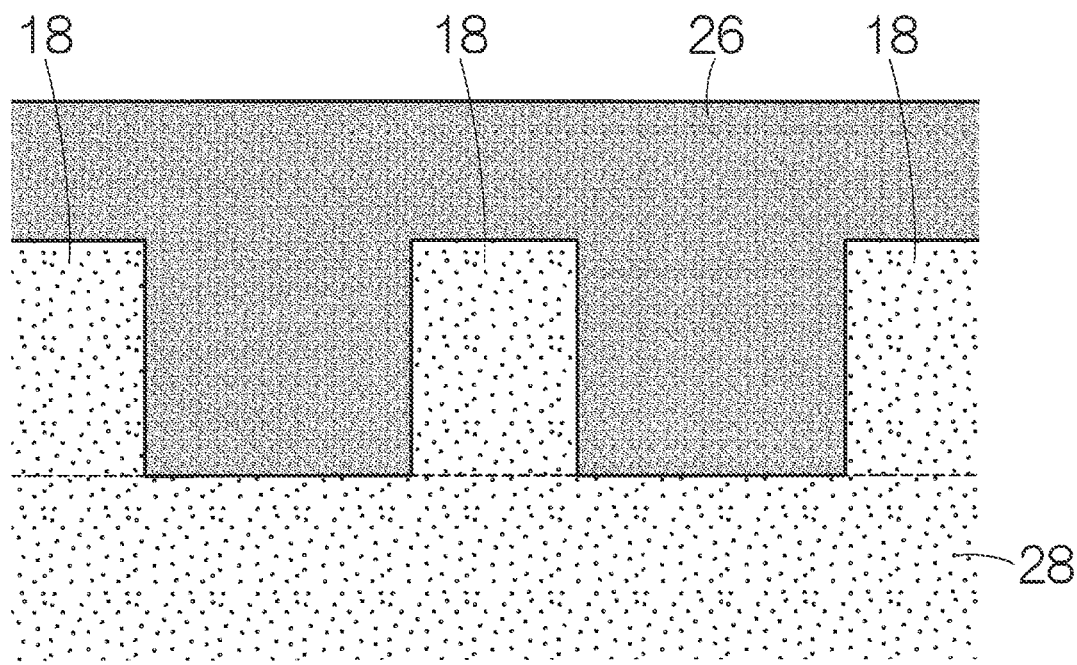
FIG. 15 is a sectional view schematically showing a molding material molded with the nickel plate.
Figure 16:
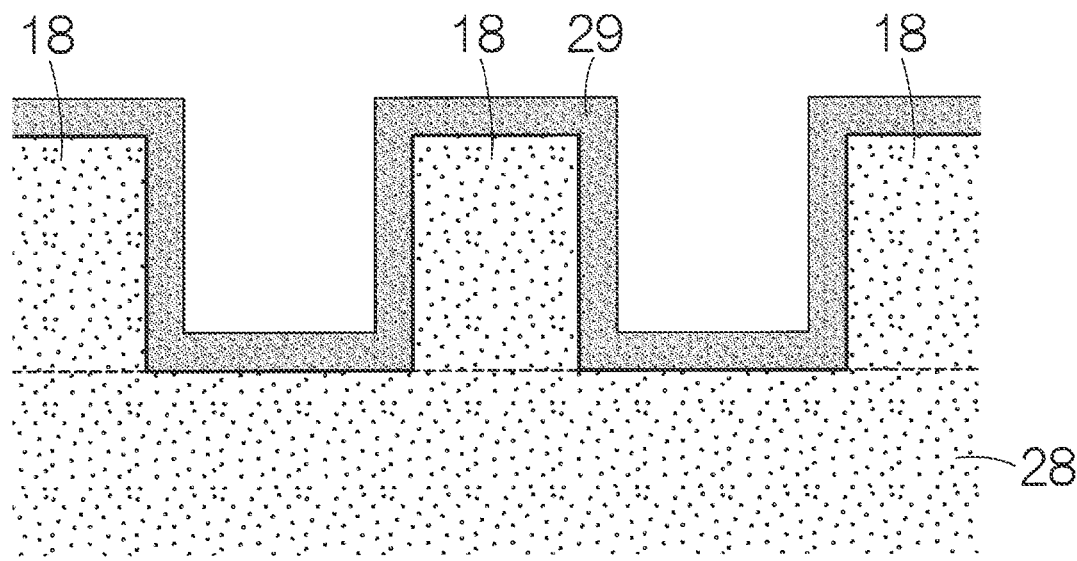
FIG. 16 is a sectional view schematically showing a metal film formed on the surface of a substrate.

As shown in FIG. 15, a substrate 28 is molded. When molding the substrate, for example, injection molding of a molding material can be used. On the surface of the substrate 28, the main bodies 18 of the nanostructures 15 are formed by integral molding. As shown in FIG. 16, a metal film 29 is formed on the entire surface of the substrate 28. When forming the metal film 29, electroless plating, sputtering, vapor deposition, or the like can be used. In this manner, the main bodies 18 which are dielectric bodies are covered with the metal film 19. The nanostructures 15 are formed. Thereafter, each substrate 12 is cut out from the substrate 28. The surface of the substrate 12 is covered with the metal film 13. The stamper can greatly contribute to the improvement of the productivity of the sample analysis device 11.

(4) Testing Apparatus According to One Embodiment

Figure 17:
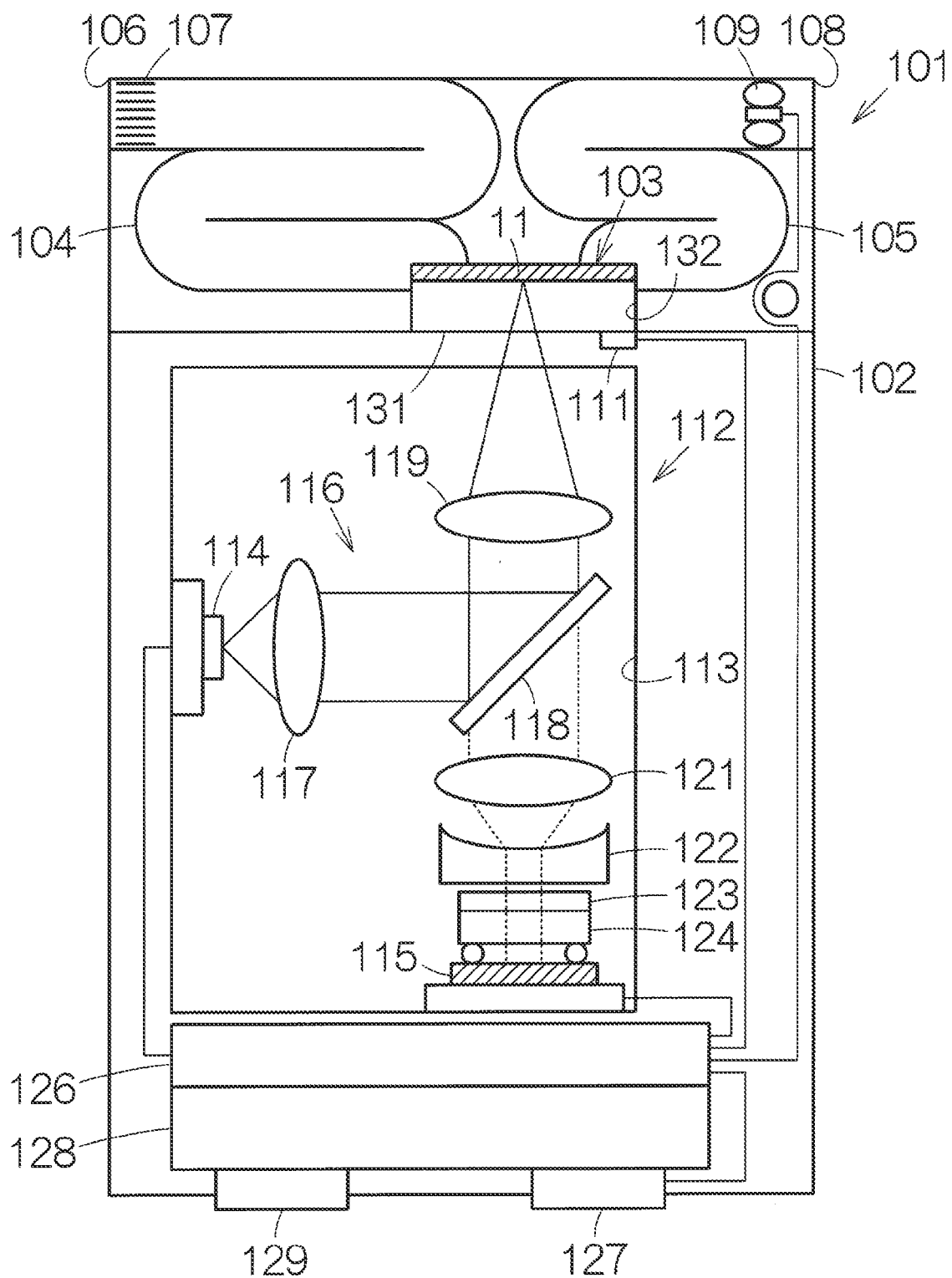
FIG. 17 is a conceptual view schematically showing the structure of a target molecule testing apparatus.

FIG. 17 schematically shows a target molecule testing apparatus (testing apparatus) 101 according to one embodiment. The target molecule testing apparatus 101 includes a housing 102. In the housing 102, a sensor cartridge 103 is incorporated. To the sensor cartridge 103, an introduction channel 104 and a discharge channel 105 are separately connected. A gas is introduced into the sensor cartridge 103 through the introduction channel 104. The gas is discharged from the sensor cartridge 103 through the discharge channel 105. A filter 107 is attached to a channel inlet 106 of the introduction channel 104. The filter 107 can remove, for example, dust or steam in the gas. A suction unit 109 is attached to a channel outlet 108 of the discharge channel 105. The suction unit 109 is composed of a ventilation fan. According to the operation of the ventilation fan, the gas is circulated through the introduction channel 104, the sensor cartridge 103, and the discharge channel 105 in this order. In such a gas circulation channel, a shutter (not shown) is placed on both upstream and downstream of the sensor cartridge 103. The gas can be confined in the sensor cartridge 103 according to opening and closing of the shutters.

In the housing 102, a discrimination sensor 111 is incorporated. The discrimination sensor 111 discriminates whether the sensor cartridge 103 is attached or detached. The discrimination sensor 111 outputs a given electrical signal according to the attachment and detachment of the sensor cartridge 103. The sensor cartridge 103 can be detachably attached to, for example, the introduction channel 104 and the discharge channel 105.

The target molecule testing apparatus 101 includes a Raman scattered light detection unit 112. The Raman scattered light detection unit 112 irradiates the sensor cartridge 103 with an excitation light and detects a Raman scattered light. In the Raman scattered light detection unit 112, a light-blocking chamber 113 is partitioned in the housing 102. The light-blocking chamber 113 is blocked from a surrounding light.

The Raman scattered light detection unit 112 includes a light source 114. The light source 114 is placed in the light-blocking chamber 113. As the light source 114, a laser light source can be used. The laser light source can emit a linearly polarized laser light at a specific wavelength (single wavelength).

The Raman scattered light detection unit 112 includes a light-receiving element 115. The light-receiving element 115 can detect, for example, a light intensity. The light-receiving element 115 can output a detected current according to the light intensity. Therefore, a light intensity can be determined according to the magnitude of a current output from the light-receiving element 115.

In the light-blocking chamber 113, an optical system 116 is constructed between the light source 114 and the sensor cartridge 103 and between the sensor cartridge 103 and the light-receiving element 115. The optical system 116 forms a light channel between the light source 114 and the sensor cartridge 103, and at the same time, forms a light channel between the sensor cartridge 103 and the light-receiving element 115. By the action of the optical system 116, a light from the light source 114 is guided to the sensor cartridge 103. A reflected light from the sensor cartridge 103 is guided to the light-receiving element 115 by the action of the optical system 116.

The optical system 116 includes a collimator lens 117, a dichroic mirror 118, an objective lens 119, a condenser lens 121, a concave lens 122, an optical filter 123, and a spectroscope 124. The dichroic mirror 118 is placed, for example, between the sensor cartridge 103 and the light-receiving element 115. The objective lens 119 is placed between the dichroic mirror 118 and the sensor cartridge 103. The objective lens 119 collects a parallel light supplied from the dichroic mirror 118 and guides the light to the sensor cartridge 103. A reflected light from the sensor cartridge 103 is converted into a parallel light by the objective lens 119 and is transmitted through the dichroic mirror 118. Between the dichroic mirror 118 and the light-receiving element 115, the condenser lens 121, the concave lens 122, the optical filter 123, and the spectroscope 124 are placed. The optical axes of the objective lens 119, the condenser lens 121, and the concave lens 122 are aligned to be coaxial with one another. The light collected by the condenser lens 121 is converted into a parallel light again by the concave lens 122. The optical filter 123 removes a Rayleigh scattered light. A Raman scattered light passes through the optical filter 123. The spectroscope 124 selectively transmits, for example, a light having a specific wavelength. In this manner, in the light-receiving element 115, the light intensity is detected at each specific wavelength. In the spectroscope 124, for example, an etalon can be used.

The optical axis of the light source 114 perpendicularly intersects the optical axes of the objective lens 119 and the condenser lens 121. The surface of the dichroic mirror 118 intersects these optical axes at an angle of 45°. The collimator lens 117 is placed between the dichroic mirror 118 and the light source 114. In this manner, the collimator lens 117 is made to face the light source 114. The optical axis of the collimator lens 117 is aligned to be coaxial with the optical axis of the light source 114.

The target molecule testing apparatus 101 includes a control unit 126. To the control unit 126, the discrimination sensor 111, the light source 114, the spectroscope 124, the light-receiving element 115, the suction unit 109, and other devices are connected. The control unit 126 controls the operation of the light source 114, the spectroscope 124, and the suction unit 109, and also processes output signals from the discrimination sensor 111 and the light-receiving element 115. To the control unit 126, a signal connector 127 is connected. The control unit 126 can exchange signals with the outside through the signal connector 127.

The target molecule testing apparatus 101 includes a power supply unit 128. The power supply unit 128 is connected to the control unit 126. The power supply unit 128 supplies an operating power to the control unit 126. The control unit 126 can operate by receiving power supply from the power supply unit 128. As the power supply unit 128, for example, a primary battery or a secondary battery can be used. The secondary battery can include, for example, a rechargeable power supply connector 129.

The control unit 126 includes a signal processing control section. The signal processing control section can be constituted by, for example, a central processing unit (CPU), and memory circuits such as a RAM (random access memory) and a ROM (read only memory). In the ROM, for example, a processing program or spectral data can be stored. With the spectral data, the spectrum of the Raman scattered light of the target molecule is determined. The CPU executes the processing program while temporarily incorporating the processing program or the spectral data in the RAM. The CPU collates the spectrum of a light to be determined by the action of the spectroscope and the light-receiving element with the spectral data.

The sensor cartridge 103 includes a housing 131. The housing 131 partitions a detection chamber 132. The detection chamber 132 is connected to the introduction channel 104 at one end and to the discharge channel 105 at the other end. In the housing 131, the sensor chip 11 is incorporated. The surface of the base body 12 is in contact with a space in the detection chamber 132. A light emitted from the light source 114 is converted into a parallel light by the collimator lens 117. A linearly polarized light is reflected by the dichroic mirror 118. The reflected light is collected by the objective lens 119 and the sensor cartridge 103 is irradiated with the light. The light is transmitted through the housing 131 of the sensor cartridge 103 and reaches the sensor chip 11. At this time, the light can be made incident in the perpendicular direction perpendicular to the surface of the sensor chip 11. So-called perpendicular incidence can be established. The polarization plane of the light is aligned parallel to the nanostructure lines 16 (first direction SD). By the action of the irradiation light, localized surface plasmon resonance is caused on the metal films 19 of the nanostructures 15. The near-field light is enhanced between the nanostructures 15. A so-called hotspot is formed.

At this time, when a target molecule adheres to the nanostructure 15 in the hotspot, a Rayleigh scattered light and a Raman scattered light are generated from the target molecule. So-called surface-enhanced Raman scattering is realized. As a result, a light is emitted to the objective lens 119 at a spectrum according to the type of the target molecule.

The light emitted from the sensor cartridge 103 in this manner is converted into a parallel light by the objective lens 119, and passes through the dichroic mirror 118, the condenser lens 121, the concave lens 122, and the optical filter 123. A Raman scattered light is incident on the spectroscope 124. The spectroscope 124 disperses the Raman scattered light. The light-receiving element 115 detects the light intensity at each specific wavelength in this manner. The spectrum of the light is collated with the spectral data. The target molecule can be detected according to the spectrum of the light. In this manner, the target molecule testing apparatus 101 can detect a target substance, for example, an adenovirus, a rhinovirus, an HIV virus, or an influenza virus based on surface-enhanced Raman scattering.

While the embodiments have been described in detail in the above description, it could be easily understood by those skilled in the art that various modifications can be made without departing in substance from the novel matter and effects of the invention. Therefore, such modifications all fall within the scope of the invention. For example, in the specification or the drawings, a term which is described at least once together with a different term having a broader meaning or the same meaning can be replaced with the different term in any parts of the specification or the drawings. Further, the structures and operations of the sample analysis device 11, the target molecule testing apparatus 101, and so on are not limited to those described in the embodiments, and various modifications can be made.

The invention claimed is:

1. A sample analysis device, comprising:
a base body; and
multiple nanostructures, which are arranged on the surface of the base body, and each of which has a dielectric body covered with a metal film, wherein
the nanostructures form multiple nanostructure lines, and in each nanostructure line, the nanostructures are arranged in a first direction at a first pitch which is smaller than the wavelength of an excitation light, and the nanostructure lines are arranged in a second direction intersecting the first direction at a second pitch which is greater than the first pitch;
wherein the second pitch is set to a dimension for establishing a first-order minimum of reflectance at a wavelength shorter than a resonance wavelength of a localized surface Plasmon resonance generated in the metal nanobodies, and further establishing a higher-order minimum than the first-order at a wavelength longer than the resonance wavelength of the localized resonance Plasmon resonance.

2. The sample analysis device according to claim 1, wherein a region which contains no nanostructures is formed between the nanostructure lines.

3. The sample analysis device according to claim 1, wherein the dielectric bodies of the nanostructures are formed integrally with the base body.

4. The sample analysis device according to claim 3, wherein the base body is formed from a molding material.

5. The sample analysis device according to claim 1, wherein the metal film covers the surface of the base body.

6. The sample analysis device according to claim 1, wherein a wavenumber at which an intersection is formed between the dispersion relations of the wavelength of a localized plasmon generated in the nanostructures arranged at the first pitch and the metal film is defined as the second pitch.

7. A testing apparatus, comprising:
the sample analysis device according to claim 1;
a light source which emits a light to the nanostructure lines; and
a light detector which detects a light emitted from the nanostructure lines according to the irradiation with the light.

8. A sensor cartridge, comprising:
a housing which partitions a detection chamber;
a base body which has a surface in contact with a space in the detection chamber; and
multiple nanostructures, which are arranged on the surface of the base body, and each of which has a dielectric body covered with a metal film, wherein
the nanostructures form multiple nanostructure lines, and in each nanostructure line, the nanostructures are arranged in a first direction at a first pitch which is smaller than the wavelength of an excitation light, and the nanostructure lines are arranged in a second direction intersecting the first direction at a second pitch which is greater than the first pitch;
wherein the second pitch is set to a dimension for establishing a first-order minimum of reflectance at a wavelength shorter than a resonance wavelength of a localized surface Plasmon resonance generated in the metal nanobodies, and further establishing a higher-order minimum than the first-order at a wavelength longer than the resonance wavelength of the localized resonance Plasmon resonance.

* * * * *